(12) United States Patent
Larsen et al.

(10) Patent No.: US 9,364,772 B2
(45) Date of Patent: Jun. 14, 2016

(54) REGENERATION OF CHROMATOGRAPHIC STATIONARY PHASES

(75) Inventors: Per Larsen, Holte (DK); Ole Schou, Stensved (DK); Eigil Schroder Rasmussen, Kobenhaven (DK)

(73) Assignee: Novo Nordisk A/S, Bagsvaerd (DK)

( * ) Notice: Subject to any disclaimer, the term of this patent is extended or adjusted under 35 U.S.C. 154(b) by 1469 days.

(21) Appl. No.: 12/098,779

(22) Filed: Apr. 7, 2008

(65) Prior Publication Data

US 2008/0312131 A1 Dec. 18, 2008

Related U.S. Application Data

(63) Continuation of application No. 11/264,345, filed on Sep. 30, 2005, now abandoned, which is a continuation of application No. PCT/DK2004/000234, filed on Apr. 2, 2004.

(30) Foreign Application Priority Data

Apr. 8, 2003 (DK) .................................. 2003 00536
Jan. 26, 2004 (DK) .................................. 2004 00098

(51) Int. Cl.
| | | |
|---|---|---|
| *B01J 20/34* | (2006.01) | |
| *B01D 15/20* | (2006.01) | |
| *C07K 1/20* | (2006.01) | |
| *B01J 20/283* | (2006.01) | |
| *B01J 20/285* | (2006.01) | |
| *B01J 20/287* | (2006.01) | |

(52) U.S. Cl.
CPC .............. *B01D 15/20* (2013.01); *B01D 15/203* (2013.01); *B01J 20/283* (2013.01); *B01J 20/285* (2013.01); *B01J 20/34* (2013.01); *B01J 20/3425* (2013.01); *B01J 20/3475* (2013.01); *C07K 1/20* (2013.01); *B01J 20/3433* (2013.01)

(58) Field of Classification Search
CPC ...... B01D 15/20; B01D 15/203; B01D 15/10; B01D 15/32; B01D 15/325; B01J 20/34; B01J 20/283; B01J 20/285; B01J 20/3475; B01J 20/342; B01J 20/281; B01J 20/287; B01J 20/3433; C07K 1/20; G01N 30/50; G01N 30/482; G01N 30/02; G01N 2030/027
USPC .......................... 210/635, 638, 656, 659, 674
See application file for complete search history.

(56) References Cited

U.S. PATENT DOCUMENTS

| | | |
|---|---|---|
| 4,164,481 A | 8/1979 | Ma et al. |
| 5,245,008 A | 9/1993 | Dickhardt et al. |
| 5,837,826 A | 11/1998 | Flickinger et al. |
| 5,977,297 A | 11/1999 | Obermeier et al. |

(Continued)

FOREIGN PATENT DOCUMENTS

| | | |
|---|---|---|
| JP | 10-221323 | 8/1998 |
| JP | 2001-133446 A | 5/2001 |

(Continued)

OTHER PUBLICATIONS

Blundell, T. L.—Lefebyre P.J.—1983—vol. 66, pp. 37-55.

(Continued)

*Primary Examiner* — Katherine Zalasky
(74) *Attorney, Agent, or Firm* — Rosemarie R. Wilk-Orescan

(57) ABSTRACT

Process for regenerating a chromatographic stationary phase.

18 Claims, 4 Drawing Sheets

After regeneration with formic acid (100%)

(56) References Cited

U.S. PATENT DOCUMENTS

| | | | |
|---|---|---|---|
| 6,191,102 | B1 | 2/2001 | DiMarchi et al. |
| 6,248,683 | B1 * | 6/2001 | Fortier et al. ............ 502/20 |
| 6,838,069 | B2 * | 1/2005 | Blonigen et al. ............ 423/352 |
| 7,052,609 | B2 | 5/2006 | Braunger et al. |
| 7,161,383 | B2 | 1/2007 | Siemers |
| 7,220,356 | B2 | 5/2007 | Thommes et al. |
| 7,396,468 | B2 * | 7/2008 | Boyes et al. ............ 210/635 |
| 2002/0049153 | A1 | 4/2002 | Bridon et al. |
| 2002/0128181 | A1 | 9/2002 | Nauck et al. |
| 2003/0006191 | A1 | 1/2003 | Heikkila et al. |
| 2004/0072332 | A1 * | 4/2004 | Suzuki ............ B01J 20/3408 435/262 |
| 2005/0005692 | A1 | 1/2005 | Giustino |
| 2005/0182257 | A1 * | 8/2005 | Antonini ............ 546/44 |

FOREIGN PATENT DOCUMENTS

| | | |
|---|---|---|
| JP | 2001-194355 A | 7/2001 |
| JP | 2006-504344 | 2/2006 |
| RU | 2239827 C1 | 11/2004 |
| SU | 1270689 A1 | 11/1986 |
| SU | 1770898 | 10/1992 |
| WO | WO 87/01038 | 2/1987 |
| WO | WO 90/12029 | 4/1990 |
| WO | WO 98/00872 | 1/1998 |
| WO | WO 99/43341 | 2/1999 |
| WO | WO 99/43361 | 2/1999 |
| WO | WO 00/41546 | 1/2000 |
| WO | WO 00/37098 | 6/2000 |
| WO | 00/61493 | 10/2000 |
| WO | WO 01/10446 | 2/2001 |
| WO | WO 01/27623 | 4/2001 |
| WO | 02/22776 A2 | 3/2002 |
| WO | WO 02/72135 | 3/2002 |
| WO | WO 02/46227 | 6/2002 |
| WO | WO 03/002136 | 1/2003 |
| WO | WO 03/103572 | 6/2003 |

OTHER PUBLICATIONS

Sendorff, R. I. et al., J. Pharm. Sci., 1998, vol. 87, pp. 183-189.
Majors, LCGC North America, vol. 21, No. 1, pp. 19-26.
O'Keefe, Journal of Chromatography A, 891, 2000, pp. 85-92.
Machine language translation of Japan Patent No. 10-221323.
Andersson, T. et al, Agarose-Based Media for High-Resolution Gel Filtration of Biopolymers, Journal of Chromatography, 1985, vol. 326, pp. 33-44.
Sievers, Dirk, Schnelle Online-Analytik Pharmakologischer Wirkstoffe in Biologischen Matrizes, Git Labor-Fachzeitschrift, 2000, vol. 44(5), pp. 633-634.
Yamamoto, Syuchi et al., Cleaning and Sterilization of Chromatographic Column, Chemical Engineering Syposium, Series 59, Food Engineering 5, 1997, pp. 20-23.
Brange et al., "Toward Understanding Insulin Fibrillation", Journal of Pharmaceutical Sciences, 1997, vol. 86, No. 5, pp. 517-525.
Kroeff et al., "Production Scale Purification of Biosynthetic Human Insulin by Reversed-Phase High-Performance Liquid Chromatography", Journal of Chromatography, 1989, vol. 461, pp. 45-61.
Blackwell et al., Fluoride-Modified Zirconium Oxide As a Biocompatible Stationary Phase for High-Performance Liquid Chromatography, Journal of Chromatography, 1991, Vol. 549, pp. 59-75.
Sanders G et al: "Psychological stress of exposure to uncontrollable noise increases plasma oxytocin in high emotionality women",Psychoneuroendocrinology 1990,vol. 15, No. 1, pp. 47-58, XP024386518.
Heldt H W et al: "Assay of nucleotides and other phosphate containing compounds in isolated chloroplasts by ion exchange chromatography", Analytical Biochemistry,1980,vol. 10,No. 2, pp. 278-287, XP024829122.
Dickinson et al. "Identification of surface residues mediating tissue factor binding and catalytic function of the serine protease factor VIIa" Proc. Natl. Acad. Sci. USA (1996) vol. 93: 14379-14384.
Liliedahl "Twelve years of silica-based HPLC purification with focus on peptides" at Tides 2000, May 10, 2000 in Las Vegas, USA.

* cited by examiner

Figure 4A-B
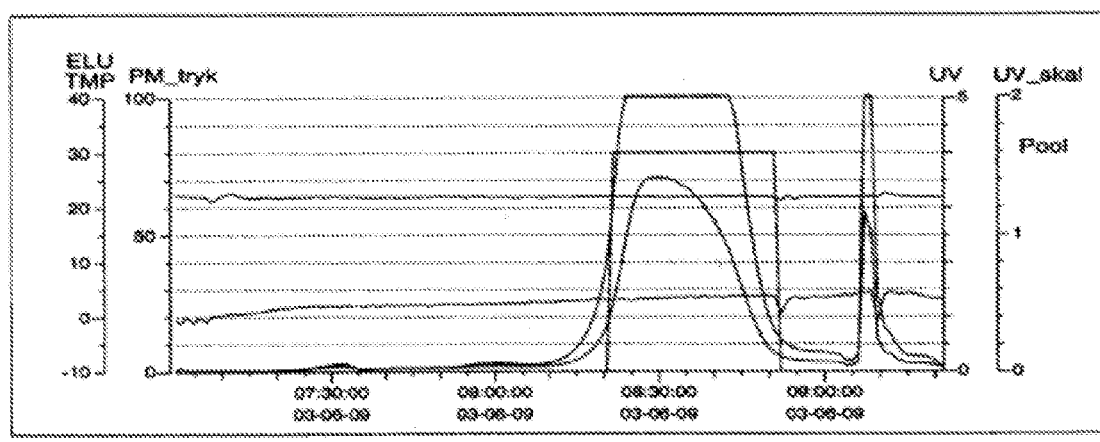
4A. Before regeneration with formic acid
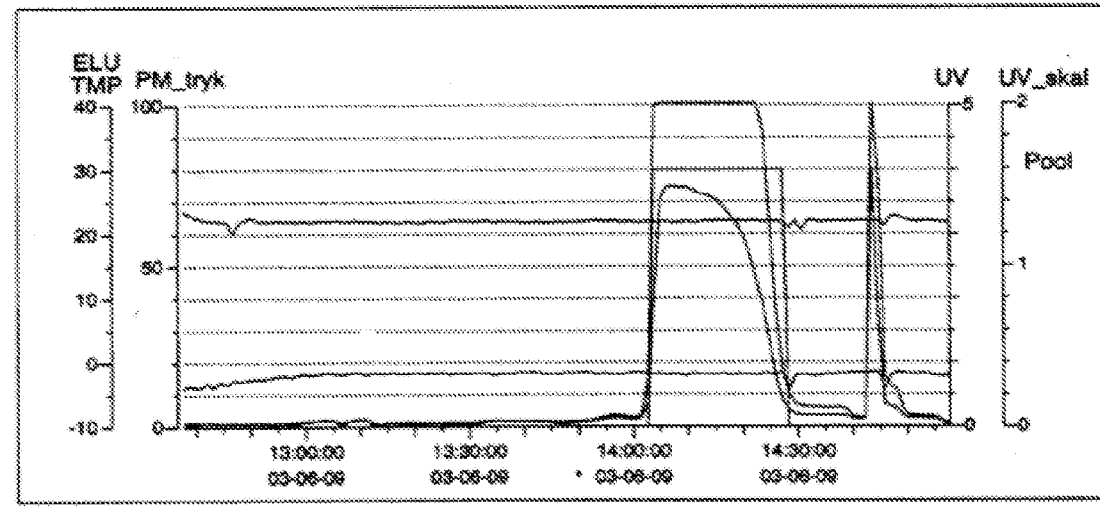
4B. After regeneration with formic acid (100%)

REGENERATION OF CHROMATOGRAPHIC STATIONARY PHASES

CROSS REFERENCE TO RELATED APPLICATIONS

This application is a continuation of U.S. application Ser. No. 11/264,345, filed Sep. 30, 2005 now abandoned, which is a continuation of International application no. PCT/DK2004/000234, filed Apr. 2, 2004, which claims priority to Danish patent application nos. PA 2003 00536, filed Apr. 8, 2003, and PA 2004 00098 filed Jan. 26, 2004 and U.S. patent application Nos. 60/462,949, filed Apr. 15, 2003 and 60/539,875 filed Jan. 27, 2004.

FIELD OF THE INVENTION

The present invention relates to the field of chromatographic purification. More specifically it pertains to a process for regenerating chromatographic stationary phases.

BACKGROUND OF THE INVENTION

Polypeptides are increasingly being used as medicaments for the treatment of diseases within all major therapy areas. Treatment of diabetes by chronic insulin administration has been practised for more than 80 years, and therapeutic applications of polypeptides within growth disorders and cancer also have been practised for many years.

Economical processes for the large scale production of polypeptides with a purity sufficiently high for therapeutic applications are crucial for further polypeptide-based therapies to reach the mass market and for the existing therapies to become more widely used.

Purification of a polypeptide from a mixture is a step which is normally used several times during the overall manufacturing process for a therapeutic polypeptide. Reverse phase high pressure liquid chromatography (RP-HPLC) is the preferred method for industrial high resolution separation of polypeptides, and the method has proven versatile for the large scale purification of many polypeptides.

Since polypeptides for therapeutic use are to be highly purified in order not to cause adverse events upon administration to the patient, it is quite common to use several chromatographic purification steps in the manufacturing process. The stationary phase of chromatographic columns in manufacturing plants are expensive and they are thus used for several chromatographic cycles. However, over time the performance of the chromatographic stationary phase declines, i.e. pressure drop over the column increases prohibitively and the separation factor is impaired. This has been attributed to the gradual build-up of deposits.

The problem has been suggested to be overcome by a regeneration process comprising alkaline buffers (J. Chrom. 461, 1989, 45-61), e.g. pH 7.4 and high concentration of organic modifier.

Brange et al. (J. Pharm. Sci. 86 (1997) 517-525) discloses dissolving insulin fibrils in acid and in base.

For many years the problem has been alleviated by regenerating the chromatographic stationary phase with alkaline solution, e.g. 0.1 molar sodium hydroxide (vide Liliedahl, "Twelve years of silica-based HPLC purification with focus on peptides", at Tides 2000, 10 May 2000 in Las Vegas, USA). This regeneration process may increase the lifetime of silica used for purifying insulin to between 100 to 600 cycles. However, silica materials are not stable when exposed to harsh alkaline conditions, and especially substituted silica materials may not be amenable to regeneration by alkaline solutions. Economically viable processes for purifying pharmaceuticals such as therapeutic polypeptides must include a regeneration process which does not degrade the chromatographic stationary phase.

A general and complex process for regenerating particulate materials (clay, sand, silica etc.) from a wide variety of sources has been disclosed in WO 00/61493. It is a 5 step process comprising contacting the material with a) an extractant of organic material, b) an oxidizing agent, followed by c) an acid solution, d) heating the material and e) recovering the material. The process is cumbersome and not amenable for implementation in a chromatographic purification plant.

There is a need in the art for more efficient ways of regenerating chromatographic stationary phases so as to increase the lifetime of these expensive raw materials and prevent the pressure drop over chromatographic columns to rise. Especially, regeneration processes which are suited for in-situ regeneration of chromatographic stationary phases in manufacturing plants are needed.

SUMMARY OF THE INVENTION

The present invention provides a process for regenerating a chromatographic stationary phase wherein said chromatographic stationary phase is contacted with a regeneration solution comprising at least one organic acid and less than about 75% w/w water.

In another aspect the present invention provides a process for regenerating a chromatographic stationary phase wherein said chromatographic stationary phase is contacted with a regeneration solution comprising at least one organic acid and less than about 1% w/w water.

In one embodiment of the invention the organic acid is formic acid. In another embodiment of the invention the organic acid is acetic acid. In another embodiment the regeneration solution contains less than 0.5% water, preferably less than 0.1% water, more preferably less than 0.02% water and most preferably less than 0.001% water.

In another aspect the present invention relates to a process for regenerating a chromatographic stationary phase wherein said chromatographic stationary phase is contacted with a regeneration solution comprising at least one organic acid, an organic solvent and less than about 1% w/w water.

In one embodiment of the invention the organic solvent is ethanol. In another embodiment of the invention the organic solvent is 2-propanol. In another embodiment of the invention the organic solvent is acetonitrile. In another embodiment of the invention the organic solvent is selected from the group consisting of methanol, 1-propanol, and hexylene glycol.

In another embodiment the regeneration solution contains less than 0.5% water, preferably less than 0.1% water, more preferably less than 0.02% water and most preferably less than 0.001% water.

In another aspect the present invention relates to a chromatographic stationary phase which has been regenerated by the processes of the invention.

In another aspect the present invention relates to a polypeptide product obtained by the processes of the invention.

In yet another aspect the present invention relates to a polypeptide product manufactured by a process comprising the regeneration of the chromatographic stationary phase by the processes.

In yet another aspect the invention relates to an automated chromatographic equipment comprising piping and control system for implementing the regeneration process.

In yet another aspect the present invention relates to a pharmaceutical composition prepared by purifying a polypeptide using a chromatographic stationary phase which has been regenerated by the process.

BRIEF DESCRIPTION OF THE DRAWINGS

The invention is further illustrated in the appended drawings in which

FIGS. 4A-B show preparative chromatograms from chromatographic purification III (FIG. 4A, upper figure, before regeneration with formic acid, and FIG. 4B (lower figure) after regeneration with formic acid).

DEFINITIONS

Figure 1:
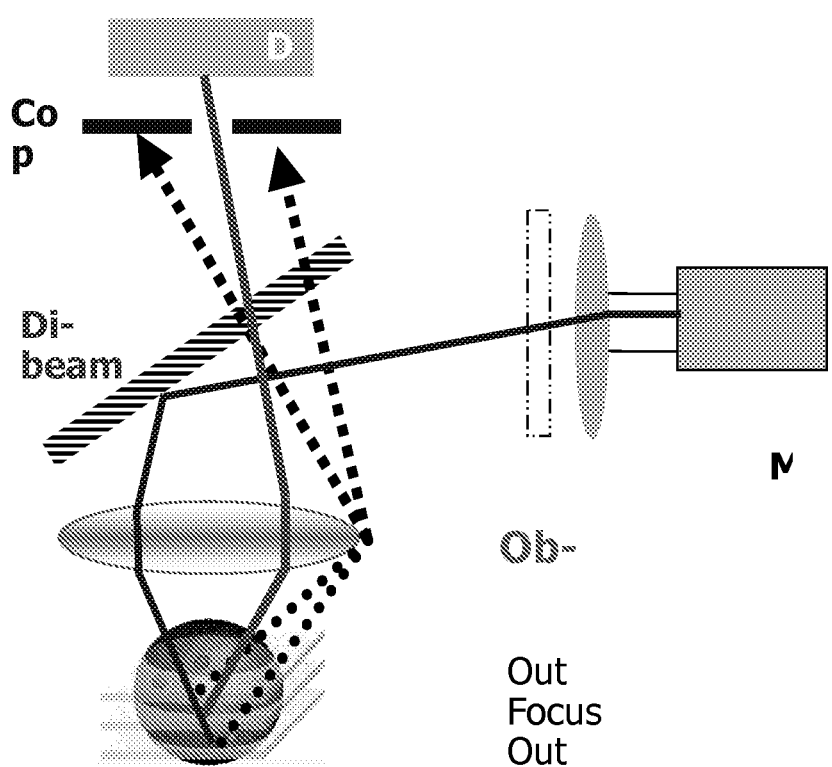
FIG. 1 shows the confocal principle.
Figure 2:
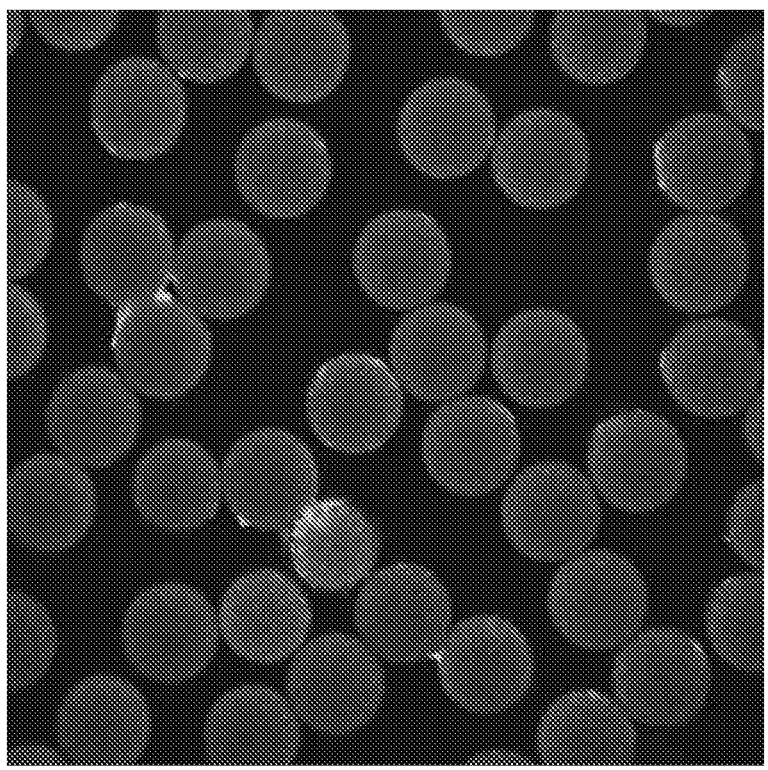
FIG. 2 shows 2D picture of Source 30Q with insulin fibrils stained with Thioflavin T.
Figure 3:
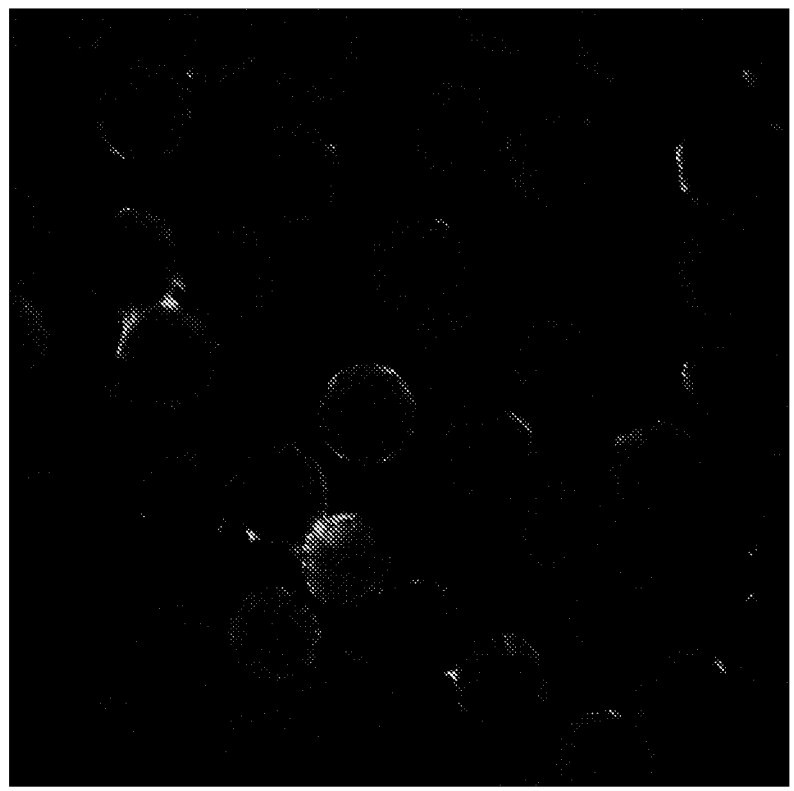
FIG. 3 shows the principle of the measuring the area of fibrils on Source 30Q. Light coloured area shows the green light coming from insulin fibrils on the Source 30Q particles.

The following is a detailed definition of the terms used in the specification.

The term "chromatographic stationary phase" as used herein means the solid phase over which the soluble phase passes, i.e. the chromatographic matrix. The chromatographic stationary phase is normally placed within a chromatographic column. Examples of chromatographic stationary phases are substituted silica, such as C-4 silica, C-12 silica and C-18 silica, as well as polymeric materials such as polystyrene, Source 30Q and Sepharose. Additional examples of chromatographic stationary phases are membranes, monolithic materials and filters.

The term "chromatographic eluent" as used herein means the solution which is used for the elution step where the polypeptide being purified is normally released from the chromatographic stationary phase into the eluent. In the normal mode of chromatography a complete cyclus comprises a) equilibration with an equilibration buffer to bring the column in a state where it is ready for a cyclus,
b) application of the product holding sample,
c) an optional washing step where the chromatographic stationary phase with the bound product is washed,
d) elution where the affinity of the product towards the chromatography stationary phase decreases and the product leaves the column in the chromatographic column eluate, and
e) an optional regeneration where it is attempted to strip the chromatographic stationary phase from remaining impurities using a regeneration solution.

The term "equilibrium buffer" as used herein means the solution which is used for the equilibration step wherein the chromatographic column is prepared for a chromatographic cycle.

The term "regeneration solution" as used herein means a solution which is used to regenerate a chromatographic stationary phase. The purpose of the regeneration is keep a satisfactory performance of the chromatographic separation over several chromatographic cycles. Typically critical performance related parameters are the pressure drop over the chromatographic column and the separation factor. A regeneration step may comprise contacting of the chromatographic stationary phase with either a single regeneration solution or with more than one regeneration solution. In the latter case, each of the regeneration solutions as well as the resulting mixtures of these are encompassed by the term "regeneration solution".

The term "mixture" as used herein means a composition of matter comprising at least two ingredients. A chromatographic column eluate is a mixture which comprises the chemicals in the eluent together with the product which has been stripped from the column. Another example of a mixture is a solution of a chemical in a solvent, e.g. saline. Yet another example of a mixture is water and a water-miscible organic solvent. Yet another example of a mixture is a solution or suspension of a polypeptide in a solvent such as water or an organic solvent The term "isolating a polypeptide" as used herein means to bring the polypeptide in a state where it is of higher concentration or higher purity than it was before isolating it, i.e. in the starting material. Thus, an example of isolating a polypeptide is to precipitate or crystallize the polypeptide from a solution and separate the precipitate or crystals from the mother liquor.

The term "organic solvent" as used herein means a solvent which comprises at least one carbon-atom and which is in the fluid state throughout the temperature range from 0° C. to 50° C. Non-limiting examples of organic solvents are lower alcohols such as methanol and ethanol, polyhydric alcohols, acetonitrile, hexane and acetone.

The term "water miscible organic solvent" as used herein means an organic solvent which has a solubility in water at 20° C. of at least 1 g/L. Non-limiting examples of water miscible organic solvents are ethanol, 1-propanol, 2-propanol, acetonitrile, and hexyleneglycol.

The term "organic acid" as used herein means an organic compound which has at least one functional group with a dissociation constant, $pK_a$, of less than 5.0. Examples of organic acids are formic acid, acetic acid, citric acid etc.

The term "lower alcohol" as used herein means a $C_{1-6}$-alcohol which is characterized by having between 1 and 6 carbon atoms and one hydroxyl moiety. The carbon skeleton in the lower alcohol may be straight or branched. Non-limiting examples of lower alcohols are ethanol, n-propanol, isopropanol, and t-butanol.

The term "polyhydric alcohol" as used herein means an alcohol having at least two hydroxyl moieties. Non-limiting examples of polyhydric alcohols are hexylene glycol (4-methyl-2,4-pentanediol) and neopentyl alcohol (2,2-dimethyl-1,3-propanediol).

The term "excipient" as used herein means compounds which are added to pharmaceutical compositions in order to stabilize and preserve the composition. Typical excipients are buffers, preservatives and tonicity modifiers.

The term "pharmaceutical composition" as used herein means a product comprising an active compound or a salt thereof together with pharmaceutical excipients such as buffer, preservative and tonicity modifier, said pharmaceutical composition being useful for treating a disease or disorder. Thus a pharmaceutical composition is also known in the art as a pharmaceutical formulation.

The term "buffer" as used herein refers to a chemical compound which is used in a solution to reduce the tendency of pH of the solution to change over time as would otherwise occur due to chemical reactions. Buffers include chemicals such as sodium phosphate, TRIS, glycine and sodium citrate.

The term "tonicity modifier" as used herein refers to a chemical compound in a pharmaceutical composition that serves to modify the osmotic pressure of the pharmaceutical composition so that the osmotic pressure becomes closer to that of human plasma. Tonicity modifiers include NaCl, glycerol, D-mannitol etc.

The term "pharmaceutically acceptable" as used herein means suited for normal pharmaceutical applications, i.e. does not cause adverse events in patients etc.

The term "human insulin" as used herein means the human hormone whose structure and properties are well known. Human insulin has two polypeptide chains that are connected by disulphide bridges between cysteine residues, namely the A-chain and the B-chain. The A-chain is a 21 amino acid peptide and the B-chain is a 30 amino acid peptide, the two chains being connected by three disulphide bridges: one between the cysteines in position 6 and 11 of the A-chain, the second between the cysteine in position 7 of the A-chain and the cysteine in position 7 of the B-chain, and the third between the cysteine in position 20 of the A-chain and the cysteine in position 19 of the B-chain.

The term "polypeptide" as used herein means a compound composed of at least ten constituent amino acids connected by peptide bonds. The constituent amino acids may be from the group of the amino acids encoded by the genetic code and they may natural amino acids which are not encoded by the genetic code, as well as synthetic amino acids. Natural amino acids which are not encoded by the genetic code are e.g. hydroxyproline, γ-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), and β-alanine.

The term "therapeutic polypeptide" as used herein means a polypeptide for which there is a recognized potential utility as a therapeutic agent. Therapeutic polypeptides are typically highly purified and they are subjected to clinical studies as part of the regulatory approval process. Examples of therapeutic polypeptides are human insulin, thrombopoetin, erythropoietin and human growth hormone.

The term "polypeptide product" as used herein means a composition comprising the polypeptide. Examples of polypeptide products are crystallized polypeptide, precipitated polypeptide, and a solution of the polypeptide.

The term "analogue" as used herein in relation to a parent polypeptide means a modified polypeptide wherein one or more amino acid residues of the parent polypeptide have been substituted by other amino acid residues and/or wherein one or more amino acid residues have been deleted from the parent polypeptide and/or wherein one or more amino acid residues have been deleted from the parent polypeptide and/ or wherein one or more amino acid residues have been added to the parent polypeptide. Such addition or deletion of amino acid residues can take place at the N-terminal of the polypeptide or at the C-terminal of the polypeptide or within the polypeptide. An example of an analogue is $Arg^{34}$-GLP-1(7-37) which is a GLP-1(7-37) polypeptide wherein the Lys at position 34 has been replaced with an Arg. Other examples are porcine or bovine insulin which are both analogues of human insulin.

The term "precursor" as used herein in relation to a polypeptide means a modified version of the polypeptide which is being produced. Precursors of a polypeptide are typically amino acid extended versions of the polypeptide, or truncated versions of the polypeptide. These precursor may serve to enhance cellular expression, comprise affinity tags for purification, protect certain reactive groups of the polypeptide being produced, etc.

The term "derivative" as used herein in relation to a parent polypeptide means a chemically modified parent polypeptide or an analogue thereof, wherein at least one substituent is not present in the parent polypeptide or an analogue thereof, i.e. a parent polypeptide which has been covalently modified. Typical modifications are amides, carbohydrates, alkyl groups, acyl groups, esters, PEGylations and the like. Examples of derivatives of human insulin are threonine methyl ester$^{B30}$ human insulin and $N^{\epsilon B29}$-tetradecanoyl des (B30) human insulin.

The term "lipophilic substituent" as used herein means a substituent comprising 4-40 carbon atoms and having a solubility in water at 20° C. in the range from about 0.1 mg/100 ml water to about 250 mg/100 ml water, such as in the range from about 0.3 mg/100 ml water to about 75 mg/100 ml water. For instance, octanoic acid (C8) has a solubility in water at 20° C. of 68 mg/100 ml, decanoic acid (C10) has a solubility in water at 20° C. of 15 mg/100 ml, and octadecanoic acid (C18) has a solubility in water at 20° C. of 0.3 mg/100 ml.

The term "piping and control system" as used herein means the physical means (pipes and control valves) and the software controlling the pipes and valves of a process equipment.

DESCRIPTION OF THE INVENTION

The present invention is concerned with a process for regenerating a chromatographic stationary phase wherein said chromatographic stationary phase is contacted with a regeneration solution comprising at least one organic acid and less than about 75% w/w water.

The present invention is also concerned with a process for regenerating a chromatographic stationary phase wherein said chromatographic stationary phase is contacted with a regeneration solution comprising at least one organic acid and less than about 1% w/w water.

The present invention is also concerned with a process for regenerating a chromatographic stationary phase wherein said chromatographic stationary phase is contacted with a regeneration solution having a concentration of organic acid which is at least 25% w/w.

A number of organic acids may be used in the regeneration solution of the process. A preferred organic acid is formic acid. Another organic acid for the regeneration solution is acetic acid. Another regeneration solution comprises two organic acids, e.g. formic acid and acetic acid.

The regeneration solution may furthermore comprise an organic solvent. Preferably the organic solvent is also used in the equilibrium buffer or chromatographic eluent. In one embodiment of the invention the organic solvent is ethanol. In another embodiment the organic solvent is 2-propanol. In another embodiment the organic solvent is acetonitrile. In another embodiment the organic solvent is selected from the group consisting of methanol, 1-propanol and hexylene glycol.

In another embodiment, the organic acid is formic acid and the organic solvent is ethanol. In another embodiment, the organic acid is formic acid and the organic solvent is acetonitrile. In yet another embodiment, the organic acid is formic acid and the organic solvent is 2-propanol. In yet another embodiment, the organic acid is formic acid and the organic solvent is hexylene glycol. In another embodiment, the organic acid is acetic acid and the organic solvent is ethanol. In another embodiment, the organic acid is acetic acid and the organic solvent is acetonitrile. In yet another embodiment, the organic acid is acetic acid and the organic solvent is 2-propanol. In yet another embodiment, the organic acid is acetic acid and the organic solvent is hexylene glycol.

In another embodiment, the present invention relates to a process for regenerating a chromatographic stationary phase wherein said chromatographic stationary phase is contacted with a regeneration solution comprising at least one organic acid and less than 0.5% water, preferably less than 0.1% water, more preferably less than 0.02% water and most preferably less than 0.001% water.

The chromatographic stationary phase is preferably contacted with the regeneration solution inside the chromatographic column. In this way a minimum of production capacity is lost due to down-time in connection with the regeneration step. Thus, the process of regenerating the chromatographic stationary phase can be performed without repacking the column. In one embodiment, the chromatographic stationary phase is fluidized during said regeneration. In another embodiment the chromatographic eluent or equilibrium buffer is displaced by a water miscible organic solvent before said chromatographic stationary phase is contacted with said regeneration solution. Preferably said water miscible organic solvent is also present in the chromatographic eluent or equilibrium buffer. Preferably said water miscible organic solvent is also present in the regeneration solution.

In another embodiment the chromatographic stationary phase is contacted with said regeneration solution outside the chromatographic column. This procedure is more cumbersome than performing the regeneration process inside the column, but it may nevertheless be useful if precipitated material is trapped between the chromatographic stationary phase particle. In the latter case, the precipitated material can be removed from the chromatographic stationary phase without dissolving said material.

In one embodiment the chromatographic stationary phase is a RP-HPLC matrix. The chromatographic stationary phase for RP-HPLC are mechanically very rigid materials which may be silica or substituted silica such as C4, C6, C8, C10, C12, C16, C18, C30 or phenyl silica, or it may be a pressure stable polymeric material which is substituted or unsubstituted. The chromatographic stationary phase, be it a silica based matrix or a polymeric material, may also be present in the columns as monolithic rods with macropores and mesopores. Suitable silica material for use as chromatographic stationary phase is spherical particles with a narrow pore size distribution and particle sizes in the range from 3 μm to 100 μm, such as from 5 μm to 100 μm, such as from 8 μm to 30 μm, such as 10 μm, 13 μm, 15 μm, 16 μm, 18 μm and 20 μm. Typically pore sizes in the range of 60 Å to 300 Å, such as 100 Å, 120 Å, 150 Å, 175 Å, 200 Å or 300 Å, are used. For pressure stable polymeric materials the pore size may be from 10 Å or even higher, e.g. 50 Å, 100 Å, 400 Å, 600 Å, 1000 Å or 3000 Å. In one embodiment the pressure stable polymeric material is Source 30Q or XAD 1180. The chromatographic column is packed with the stationary phase and after appropriate testing of the quality of the packing, the column is equilibrated with the buffer used in the binding mode. Production scale chromatographic columns typically have diameters of 15 to 100 cm, and such systems may have dynamic axial compression. For production of small volume polypeptides the production columns may have a diameter of e.g. 15 cm, 20 cm or 25 cm. For production of large volume polypeptides the production columns may have a diameter of e.g. 40 cm, 60 cm, 80 cm or larger.

In another embodiment of the invention, the chromatographic stationary phase being regenerated is a membrane, monolithic materials, filters or the like.

In one embodiment of the process for regenerating a chromatographic stationary phase, said chromatographic stationary phase is contacted with said regeneration solution for at least 1 second, preferably for at least 1 minute, more preferably for at least 5 minutes, such as from 1 minute to 24 hours, from 1 minute to 5 hours, from 1 minute to 2 hours, from 10 minutes to 60 minutes.

In another embodiment of the process for regenerating a chromatographic stationary phase, said chromatographic stationary phase is contacted with said regeneration solution until the pressure drop over the length of the chromatographic column at normal flow rate decreases by at least 10%, preferably at least 25%, even more preferably at least 50%.

In another embodiment of the process for regenerating a chromatographic stationary phase, contacting of said chromatographic stationary phase with the regeneration solution is performed at a temperature in the range from about 0° C. to 70° C., from 5° C. to 50° C., such as from 10° C. to 40° C., such as from 15° C. to 30° C., or from 18° C. to 25° C.

In another embodiment of the process for regenerating a chromatographic stationary phase, the life time of said chromatographic stationary phase is at least 500 chromatographic cycles, preferably at least 700 chromatographic cycles, more preferably at least 1000 chromatographic cycles, most preferably at least 2000 chromatographic cycles.

In another embodiment of the process for regenerating a chromatographic stationary phase, said process is applied to said chromatographic stationary phase for every chromatographic cycle, at least once every 2 chromatographic cycles, at least once every 5 chromatographic cycles, at least once every 20 chromatographic cycles, at least once every 50 chromatographic cycles, or at least once every 100 chromatographic cycles.

In another embodiment of the invention, the number of regeneration processes performed on a chromatographic stationary phase is at least 25, at least 50, at least 100, at least 200, at least 400 or at least 1000.

In another embodiment of the process for regenerating a chromatographic stationary phase, said process is applied to said chromatographic stationary phase whenever the pressure drop over the length of the chromatographic column exceeds a threshold value.

Another aspect of the present invention is a process for the production of a therapeutic polypeptide or a precursor thereof, said process comprising at least one chromatographic step wherein the chromatographic stationary phase is regenerated by a regeneration process as described above. In one embodiment of the process for the production of a therapeutic polypeptide or a precursor thereof, said therapeutic polypeptide is a derivative comprising a lipophilic substituent. In another embodiment of the process for the production of a therapeutic polypeptide or a precursor thereof, said therapeutic polypeptide is a derivative comprising a lipophilic substituent attached to the ϵ-amino group of a lysine residue. In another embodiment of the process for the production of a therapeutic polypeptide or a precursor thereof, said therapeutic polypeptide is selected from the group consisting of glucagon, glucagon-like peptide 1, glucagon-like peptide 2, exendin-4, TFF peptides, human insulin, analogues thereof and derivatives thereof. In another embodiment said polypeptide is selected from the group consisting of $Lys^{26}(N^{\epsilon}$-($\gamma$-Glu ($N^{\alpha}$-hexadecanoyl)))-GLP-1(7-37), $Arg^{34}$-GLP-1(7-37), exendin-4, $Lys^{17}Arg^{30}$-GLP-2(1-33), $Arg^{30}Lys^{17}N^{\epsilon}$($\beta$-Ala ($N^{\alpha}$-hexadecanoyl)) GLP-2(1-33) and $Gly^{2}$-GLP-2(1-33). In another embodiment said polypeptide is exendin-4. In another embodiment said polypeptide is a fusion polypeptide comprising human serum albumin or a fragment thereof. In another embodiment said polypeptide is a fusion polypeptide between GLP-1(7-37) or an analogue thereof and a human serum albumin fragment or an analogue thereof. In another embodiment said polypeptide is a fusion polypeptide between exendin-4(1-39) or an analogue thereof and a human serum albumin fragment or an analogue thereof. In another embodiment said polypeptide is a fusion polypeptide comprising the Fc portion of an immunoglobulin or a fragment thereof. In another embodiment said polypeptide is a fusion polypeptide between GLP-1 (7-37) or an analogue thereof and a fragment of the Fc portion of an immunoglobulin or an analogue thereof. In another embodiment said polypeptide is a fusion polypeptide between exendin-4(1-39) or an analogue thereof and a fragment of the Fc portion of an immunoglobulin or an analogue thereof.

In another embodiment said polypeptide is selected from the group consisting of human insulin, a human insulin precursor, a human insulin analog, a human insulin analog precursor, a GLP-1(7-37) analogue, an exendin-4(1-39) analogue, and derivatives thereof. In another embodiment said polypeptide is selected from a human insulin derivative comprising at least one methoxy or ethoxy moiety. In another embodiment said polypeptide is selected from the group consisting of threonine methyl ester$^{B30}$ human insulin,
threonine ethyl ester$^{B30}$ human insulin,
Asp$^{B28}$ human insulin,
threonine methyl ester$^{B30}$ Asp$^{B23}$ human insulin,
threonine ethyl ester$^{B30}$ Asp$^{B23}$ human insulin,
Lys$^{B23}$ Pro$^{B29}$ human insulin,
Met$^{B-1}$Arg$^{B0}$Lys$^{B28}$ Pro$^{B29}$ human proinsulin,
Lys$^{B3}$ Glu$^{B29}$ human insulin,
Gly$^{A21}$ Arg$^{B31}$ Arg$^{B32}$ human insulin,
des(B30) human insulin,
N$^{\epsilon B29}$-tetradecanoyl des(B30) human insulin,
N$^{\epsilon B29}$-litocholoyl-γ-glutamyl des(B30) human insulin,
N$^{\epsilon B29}$-octanoyl des(B30) human insulin, and.
N$^{\epsilon B29}$-octanoyl human insulin.

In yet another embodiment said polypeptide is selected from human serum albumin, erythropoietin, TNF-α, an interleukin, IGF-1, IGF-2, human growth hormone, somatostatin, human amylin and analogues thereof.

The polypeptides being purified on chromatographic stationary phases regenerated by the processes of the present invention may be produced by a variety of techniques known in the art of polypeptide production. Polypeptides larger than 3000 Dalton are usually produced by fermentation or cell culture, whereas smaller polypeptide may be produced by chemical peptide synthesis. Other important factors determining the optimal production method are also the amount of polypeptide to be produced and the structure of the polypeptide, e.g. disulphide bonds and other modifications. Fermentation or cell culture derived polypeptides are commonly produced by cultivation of recombinant host cells, e.g. bacteria, fungi mammalian cells, insect cells or plant cells in appropriate cultivation media. The cultivation medium may be a more or less chemically defined medium containing the necessary nutrients for growth and product formation of the host cells, e.g. sugar, nitrogen source, salts, vitamins and other growth factors. Once the microorganisms or the cells have been cultivated in the medium and they have optionally been disrupted, the cultivation medium contains the desired product in a mixture with remnant medium components, host cell derived impurities and product related impurities. Host cell derived impurities are mainly polypeptides, nucleic acids and cellular debris. The product is separated from these non-related impurities in the recovery or early purification steps. In the final purification steps (polishing) where impurities closely related to the product polypeptide are separated from the product polypeptide, chromatographic steps are extensively used.

Synthesis of polypeptides may also be performed via solid phase synthesis by Merrifield-type chemistry, by solution phase methods, or by semisynthetic methods known in the art. One or more chemical conversion steps may be performed in-between the recovery and the final purification steps. Such chemical modifications may by the hydrolysis of a precursor polypeptide wherein the amino acid extension on the polypeptide is cleaved of the polypeptide. Such amino acid extensions may be used for increasing the host cell expression in the case of culture derived polypeptides, or it may be used to specifically purify the polypeptide, such as by affinity chromatography e.g. IMAC purification of histidine tagged polypeptides. The chemical conversion can also be the chemical modification to produce a polypeptide which is a derivative, e.g. by acylation, PEGylation or esterification. Such chemical modifications are well known in the art (see e.g. WO 98/08871, WO 99/43706, U.S. Pat. No. 5,424,286, WO 00/09666, WO 00/66629, WO 01/04156 and WO 02/90388).

Another aspect of the present invention is the use of the above processes for regenerating a chromatographic stationary phase for decreasing the pressure drop over the length of the chromatographic column.

Another aspect of the present invention is the use of the above processes for regenerating a chromatographic stationary phase for the manufacture of a therapeutic polypeptide.

Another aspect of the present invention is a chromatographic stationary phase which has been regenerated by contacting said chromatographic stationary phase with a regeneration solution, said regeneration solution comprising at least one organic acid and less than about 75% w/w water. Another aspect of the present invention is a chromatographic stationary phase which has been regenerated by contacting said chromatographic stationary phase with a regeneration solution, said regeneration solution comprising at least one organic acid and less than about 1% w/w water.

In one embodiment the chromatographic stationary phase has been regenerated by a process as described above. In another embodiment the chromatographic stationary phase has been regenerated by a process, wherein said regeneration solution contains less than 0.5% water, preferably less than 0.1% water, more preferably less than 0.02% water and most preferably less than 0.001% water. In a further embodiment the regenerated chromatographic stationary phase is a silica, or a substituted silica material.

In another aspect the present invention relates to a polypeptide product manufactured by a process comprising the steps of a) purifying a polypeptide or a precursor thereof using the chromatographic stationary phase produced by the regeneration process of the present invention, and b) isolating said polypeptide or a precursor thereof to give the resulting polypeptide product.

In another aspect the present invention relates to a polypeptide product manufactured by a process wherein is used a chromatographic stationary phase regenerated according to the process of the present invention.

In another aspect the present invention relates to an automated chromatographic equipment comprising piping and control system for implementing the regeneration process according to the present invention.

In another aspect the present invention relates to a pharmaceutical composition prepared by a process comprising the steps of a) first purifying a polypeptide or a precursor thereof using a chromatographic stationary phase regenerated by the process according to the present invention,
b) then drying said polypeptide, and
c) finally admixing with a pharmaceutically acceptable excipient.

In another aspect the present invention relates to a pharmaceutical composition prepared by a process comprising the steps of
a) first purifying a polypeptide or a precursor thereof using a chromatographic stationary phase regenerated by the process wherein said chromatographic stationary phase is contacted with a regeneration solution comprising at least one organic acid and less than 0.5% water, preferably less than 0.1% water, more preferably less than 0.02% water and most preferably less than 0.001% water, and
b) then drying said polypeptide, and
c) finally admixing with a pharmaceutically acceptable excipient.

EXAMPLES

The following acronyms for commercially available chemicals and materials are used
HCOOH: Formic acid
EtOH: Ethanol
AcOH: Acetic acid
ODDMS: Octadecyldimethyl substituted silica particles (ODDMS silica)

The formic acid used for examples 1-68, 70-71, 73-74 and 76 has a specified purity of 98-100% (according to manufacturer), and the formic acid used for example 72 has a purity of 99.9%.

The abbreviation CV means Column Volumes as known in the field of chromatography.

Example 1-68

The over all set-up of the experiments of example 1-68 was as follows:
1) Determination of the back pressure and height of valley of a column with no pressure problems (a new unused column).
2) Introduction of pressure and performance problems.
3) Determination of the back pressure and height of valley of a column with pressure problems.
4) Regeneration of the column.
5) Determination of the back pressure and height of valley of a column after regeneration.

Determination of the Back Pressure and Height of Valley:

The same type of silica gel was used for all the experiments mentioned in this section. The silica gel is an ODDMS 200 Å, 15 μm silica gel. Mostly, the same gel batch (batch no. 205144) was used (all the columns starting with 874-).

The silica gel was packed in 10 mm×250 mm steel columns and tested in a functionality test using DesB30 insulin as the test substance and eluting with water-ethanol mixtures containing calcium chloride and potassium chloride salts (see table 1). The back pressure under elution and the height of valley between DesB30 insulin and the nearest impurity (in front of the insulin peak) were used as the test parameters for how well the column had regained its performance.

The elution time of DesB30 insulin may be subject to some experimental variation due to small variations in temperature and other experimental parameters. When the elution time of DesB30 insulin is the same in different experiments the height of valley is a perfect comparison of the columns separation performance. When the elution time of DesB30 insulin varies between experiments the height of valley is a less good measure of the column separation performance. All else equal, the longer the retention time is the lower the height of valley will be.

TABLE 1

Solutions used in the functionality test.

| Inlet | Buffer | Type | Content (w/w) |
|---|---|---|---|
| A11 | 1 | Equilibration buffer | 20% ethanol |
| A12 | 2 | Elution buffer A | 25% ethanol, 1.5% KCl, 0.4% $CaCl_2$ and 0.15% triethanol amine (pH 7.4 with HCl) |
| B1 | 3 | Elution buffer B | 35% ethanol, 1.5% KCl, 0.4% $CaCl_2$ and 0.15% triethanol amine (pH 7.4 with HCl) |
| A13 | 4 | Regeneration buffer | 70% ethanol and 6.9% acetic acid |
| A18 | Application | DesB30 insulin | $Na_2EDTA$ solution, pH 7.5, ethanol |

The functionality test was performed at 23±2° C. on an Äktaexplorer 100A with Unicorn 4.0 as the control software and running the following column cycle (see table 2):

TABLE 2

Column cycle in the functionality test (CV is column volumes).

| Action | CV (no.) | Volume (ml) |
|---|---|---|
| Equilibration | 3 | 58.9 |
| Loading | 0.8 | 15 |
| Wash 1 | 1 | 19.6 |
| Elution | 10 | 196.3 |
| Wash 2 | 0.5 | 9.8 |
| Rinse | 2 | 39.3 |

A column packed with silica gel (batch 205144) was tested and the back pressure measured to 3.4±0.1 MPa. Similarly the back pressure was determined for other columns before introducing pressure problems. Experiments show that if these values are regained after treatment, the column has regained its performance.

The height of valley was also determined for the individual columns before and after introduction of pressure and performance problems, and after regeneration of the column.

Introduction of Pressure and Performance Problems:

Pressure and performance problems were introduced in 1 of 3 ways
1) The column was used in the functionality test but was taken off the system after loading and placed at 70° C. for 1-16 hours. Thereafter the back pressure and height of valley were measured performing the rest of the functionality test.
2) The ODDMS silica gel (25 g) was stirred in a beaker with DesB30 insulin (0.14 g), 0.1M Tris buffer (22 ml) and ethanol (15 ml) at 50° C. for 1 hour. Thereafter the gel was decanted and packed in a steel column (10 mm×250 mm). The backpressure and height of valley were measured performing the functionality test.
This method can also be performed at lower temperatures but that demands longer reaction times.
3) A combination of 1) and 2). Firstly, the gel was treated as in 2) but after packing, the column was treated as in 1).

The methods used for the individual columns are listed in table 4 below.

Regeneration of the Column (e.i. Removal of Pressure and Performance Problems):

The regeneration of the column was also performed on the Äktaexplorer 100A. The column cycle for this process can be seen in table 3 below. After regeneration, the column was again tested in the functionality test and the back pressure determined.

TABLE 3

Column cycle under regeneration.

| Action | Solvent | CV (no.) | Volume (ml) |
|---|---|---|---|
| Wash 1 | EtOH | 3 | 58.9 |
| Regeneration | See table 4 and 5 | 2 | 39.3 |
| Left to stand | — | 0 | 30 minutes |
| Regeneration | See table 4 and 5 | 2 | 39.3 |
| Wash 2 | EtOH | 3 | 58.9 |

Different solvents were tested at 22° C. and 40° C. (the entire HPLC system was placed in a refrigerator at the chosen temperature±1° C.). The specific conditions for the individual columns are shown in table 4 and the results from the functionality tests are shown in table 5.

Specific Experimental Conditions for the Individual Columns:

TABLE 4

Experimental conditions for individual columns.

| Example no. | Column no. | Introduction of problems by method no. | Regeneration solvent | Temperature (° C.) |
|---|---|---|---|---|
| 1 | 204377/1 | 1 | HCOOH | 22 |
| 2 | 874-32/1 | 2 | HCOOH | 22 |
| 3 | 874-32/2 | 3 | HCOOH | 22 |
| 4 | 874-32/7 | 2 | HCOOH | 22 |
| 5 | 874-33/9 | 2 | HCOOH | 22 |
| 6 | 874-33/6 | 3 | HCOOH | 22 |
| 7 | 874-24/22 | 2 | HCOOH | 40 |
| 8 | 874-24/10 | 3 | AcOH | 22 |
| 9 | 874-24/15 | 2 | AcOH | 22 |
| 10 | 874-24/23 | 2 | AcOH | 40 |
| 11 | 874-31/1 | 2 | AcOH | 40 |
| 12 | 203635/5 | 1 | HCOOH/AcOH 99:1 | 22 |
| 13 | 874-24/6 | 3 | HCOOH/AcOH 99:1 | 22 |
| 14 | 205019/1 | 1 | HCOOH/AcOH 99:1 | 40 |
| 15 | 204770/1 | 1 | HCOOH/AcOH 3:1 | 22 |
| 16 | 874-24/26 | 2 | HCOOH/AcOH 3:1 | 40 |
| 17 | 204888/1 | 1 | HCOOH/AcOH 1:1 | 22 |
| 18 | 874-24/27 | 2 | HCOOH/AcOH 1:1 | 40 |
| 19 | 204923/1 | 1 | HCOOH/AcOH 1:3 | 22 |
| 20 | 874-24/28 | 2 | HCOOH/AcOH 1:3 | 40 |
| 21 | 203251/3 | 1 | HCOOH/EtOH 99:1 | 22 |
| 22 | 874-24/4 | 2 | HCOOH/EtOH 99:1 | 22 |
| 23 | 204815/1 | 1 | HCOOH/EtOH 99:1 | 40 |
| 24 | 204815/1 | 1 | HCOOH/EtOH 3:1 | 22 |
| 25 | 204888/1 | 1 | HCOOH/EtOH 3:1 | 40 |
| 26 | 874-24/5 | 3 | HCOOH/EtOH 1:1 | 22 |
| 27 | 874-24/16 | 2 | HCOOH/EtOH 1:1 | 22 |
| 28 | 204923/1 | 1 | HCOOH/EtOH 1:1 | 40 |
| 29 | 204550/1 | 1 | HCOOH/EtOH 1:3 | 22 |
| 30 | 874-24/17 | 2 | HCOOH/EtOH 1:3 | 22 |
| 31 | 204770/1 | 1 | HCOOH/EtOH 1:3 | 40 |
| 32 | 203635/5 | 1 | HCOOH/water 99:1 | 22 |
| 33 | 874-24/24 | 2 | HCOOH/water 99:1 | 40 |
| 34 | 204377/1 | 1 | HCOOH/water 95:5 | 22 |
| 35 | 874-24/29 | 2 | HCOOH/water 95:5 | 40 |
| 36 | 202985/2 | 1 | HCOOH/water 4:1 | 22 |
| 37 | 874-24/30 | 2 | HCOOH/water 4:1 | 40 |
| 38 | 204550/1 | 1 | HCOOH/water 1:1 | 22 |
| 39 | 874-24/31 | 2 | HCOOH/water 1:1 | 40 |
| 40 | 874-33/5 | 3 | HCOOH/water 1:1 | 40 |
| 41 | 874-24/7 | 3 | HCOOH/water 1:3 | 22 |
| 42 | 874-24/18 | 2 | HCOOH/water 1:3 | 22 |
| 43 | 204770/1 | 1 | HCOOH/water 1:3 | 40 |
| 44 | 874-24/8 | 3 | AcOH/water 99:1 | 22 |
| 45 | 874-24/19 | 2 | AcOH/water 99:1 | 40 |
| 46 | 874-24/11 | 3 | AcOH/water 3:1 | 22 |
| 47 | 874-24/20 | 2 | AcOH/water 3:1 | 40 |
| 48 | 874-31/2 | 2 | AcOH/water 3:1 | 40 |
| 49 | 874-33/4 | 3 | AcOH/water 3:1 | 40 |
| 50 | 874-24/12 | 3 | AcOH/water 1:1 | 22 |
| 51 | 874-24/25 | 2 | AcOH/water 1:1 | 40 |
| 52 | 874-31/3 | 2 | AcOH/water 1:1 | 40 |
| 53 | 874-24/13 | 3 | HCOOH/phenol/water 1:1:1 | 22 |
| 54 | 874-24/21 | 2 | HCOOH/phenol/water 1:1:1 | 22 |
| 55 | 874-32/3 | 2 | 1500 ppm Na-hypochlorite | 22 |
| 56 | 874-33/11 | 3 | 1500 ppm Na-hypochlorite | 22 |
| 57 | 874-33/14 | 2 | 1500 ppm Na-hypochlorite | 22 |
| 58 | 874-32/4 | 2 | Performic acid | 22 |
| 59 | 874-33/13 | 3 | Performic acid | 22 |
| 60 | 874-33/18 | 2 | Performic acid | 22 |
| 61 | 874-32/5 | 2 | 1.5M formaldehyde | 22 |
| 62 | 874-33/12 | 3 | 1.5M formaldehyde | 22 |
| 63 | 874-33/15 | 2 | 1.5M formaldehyde | 22 |
| 64 | 874-32/6 | 2 | 6M guanidine hydrochloride | 22 |
| 65 | 874-33/10 | 3 | 6M guanidine hydrochloride | 22 |
| 66 | 874-33/17 | 2 | 6M guanidine hydrochloride | 22 |
| 67 | 874-33/19 | 2 | EtOH (60% w/w)/ 0.1M NaOH | 22 |
| 68 | 874-33/20 | 3 | EtOH (60% w/w)/ 0.1M NaOH | 22 |

Functionality Test Results for the Individual Columns:

TABLE 5

Back pressure and height of valley results from functionality tests performed before and after introduction of problems and after regeneration of the columns according to the conditions listed in table 4.
RT is the retention time for DesB30 insulin and height of valley (HV) is for DesB30 insulin and the nearest impurity.

| | Back pressure (MPa) | | | Performance | | | | | |
|---|---|---|---|---|---|---|---|---|---|
| | | | | Before problems | | After problems | | After regeneration | |
| Example no. | Before problems | After problems | After regeneration | RT ml | HV mAU | RT ml | HV mAU | RT ml | HV mAU |
| 1 | 3.8 | 6.2 | 3.8 | 140.2 | 38.4 | | | 144.3 | 36.1 |
| 2 | 3.4 | 5.8 | 3.6 | 141.2 | 39.6 | 146.6 | 62.0 | 138.6 | 44.5 |

TABLE 5-continued

Back pressure and height of valley results from functionality tests performed before and after introduction of problems and after regeneration of the columns according to the conditions listed in table 4.
RT is the retention time for DesB30 insulin and height of valley (HV) is for DesB30 insulin and the nearest impurity.

| | Back pressure (MPa) | | | Performance | | | | | |
|---|---|---|---|---|---|---|---|---|---|
| | | | | Before problems | | After problems | | After regeneration | |
| Example no. | Before problems | After problems | After regeneration | RT ml | HV mAU | RT ml | HV mAU | RT ml | HV mAU |
| 3 | 3.4 | >10 | 3.7 | 141.2 | 39.6 | — | — | 137.9 | 45.9 |
| 4 | 3.4 | 4.4 | 3.4 | 141.2 | 39.6 | 146.6 | 62.0 | 139.0 | 43.2 |
| 5 | 3.4 | 4.7 | 3.4 | 141.7 | 41.9 | 134.6 | 63.0 | 139.2 | 42.9 |
| 6 | 3.4 | >10 | 3.6 | 141.7 | 41.9 | — | — | 140.1 | 45.8 |
| 7 | 3.4 | 4.7 | 3.4 | 134.5 | 54.3 | 136.5 | 47.8 | 137.2 | 48.6 |
| 8 | 3.4 | >10 | >10 | 134.5 | 54.3 | — | — | — | — |
| 9 | 3.4 | 4.7 | 4.4 | 134.5 | 54.3 | 136.5 | 47.8 | 135.9 | 48.4 |
| 10 | 3.4 | 4.7 | 3.9 | 134.5 | 54.3 | 136.5 | 47.8 | 135.0 | 50.1 |
| 11 | 3.4 | 4.2 | 4.2 | 134.5 | 54.3 | | | 149.5 | 44.7 |
| 12 | 3.0 | 3.7 | 2.8 | 136.1 | 42.7 | | | 130.3 | 51.9 |
| 13 | 3.4 | >10 | 3.5 | 134.5 | 54.3 | — | — | 145.2 | 44.4 |
| 14 | 3.5 | >10 | 3.5 | 139.9 | 44.1 | — | — | 135.9 | 44.8 |
| 15 | 3.5 | >10 | 3.3 | 138.7 | 40.6 | — | — | 127.3 | 54.7 |
| 16 | 3.4 | 4.7 | 3.4 | 134.5 | 54.3 | 136.5 | 47.8 | 139.3 | 45.0 |
| 17 | 3.0 | >10 | 2.9 | 139.2 | 30.4 | — | — | 130.2 | 36.2 |
| 18 | 3.4 | 4.7 | 3.4 | 134.5 | 54.3 | 136.5 | 47.8 | 137.1 | 47.0 |
| 19 | 3.1 | >10 | 3.0 | 130.2 | 36.2 | — | — | 133.3 | 57.2 |
| 20 | 3.4 | 4.7 | 3.5 | 134.5 | 54.3 | 136.5 | 47.8 | 136.6 | 47.5 |
| 21 | 2.2 | 3.4 | 2.3 | 131.6 | 32.9 | | | 133.8 | 35.2 |
| 22 | 3.4 | 5.2 | 3.4 | 134.5 | 54.3 | 136.5 | 47.8 | 135.1 | 50.1 |
| 23 | 3.4 | 5.8 | 3.3 | 148.5 | 29.6 | | | 142.0 | 65.0 |
| 24 | 3.3 | 6.2 | 3.1 | 135.2 | 35.4 | | | 135.3 | 34.0 |
| 25 | 3.1 | 9 | 3.1 | 157.0 | 24.7 | — | — | 151.3 | 31.9 |
| 26 | 3.4 | >10 | >10 | 134.5 | 54.3 | — | — | — | — |
| 27 | 3.4 | 4.7 | 3.5 | 134.5 | 54.3 | 136.5 | 47.8 | 136.2 | 46.9 |
| 28 | 3.2 | >10 | 3.5 | 139.7 | 44.7 | — | — | 148.0 | 35.7 |
| 29 | 2.8 | >10 | >10 | 142.4 | 23.2 | — | — | — | — |
| 30 | 3.4 | 4.7 | 4.1 | 134.5 | 54.3 | 136.5 | 47.8 | 137.6 | 44.2 |
| 31 | 3.6 | >10 | >10 | 147.4 | 38.7 | — | — | — | — |
| 32 | 3.1 | 6.9 | 3.1 | 143.8 | 34.7 | | | 136.3 | 41.4 |
| 33 | 3.4 | 4.7 | 3.3 | 134.5 | 54.3 | 136.5 | 47.8 | 132.1 | 55.8 |
| 34 | 3.7 | >10 | 3.9 | 140.6 | 41.6 | — | — | 145.8 | 34.5 |
| 35 | 3.4 | 4.7 | 3.6 | 134.5 | 54.3 | 136.5 | 47.8 | 139.8 | 42.0 |
| 36 | 2.4 | 5.1 | 2.3 | 145.8 | 22.0 | | | 134.1 | 32.0 |
| 37 | 3.4 | 4.7 | 3.5 | 134.5 | 54.3 | 136.5 | 47.8 | 140.3 | 45.4 |
| 38 | 2.6 | 4.6 | 2.7 | 126.6 | 27.2 | | | 135.9 | 34.5 |
| 39 | 3.4 | 4.7 | 3.4 | 134.5 | 54.3 | 136.5 | 47.8 | 140.4 | 42.2 |
| 40 | 3.4 | >10 | 4.1 | 141.7 | 41.9 | — | — | 141.8 | 64.0 |
| 41 | 3.4 | >10 | >10 | 134.5 | 54.3 | — | — | — | — |
| 42 | 3.4 | 4.7 | 3.3 | 134.5 | 54.3 | 136.5 | 47.8 | 137.0 | 45.6 |
| 43 | 3.4 | 5.8 | 3.8 | 131.9 | 47.0 | | | 145.0 | 40.8 |
| 44 | 3.4 | >10 | >10 | 134.5 | 54.3 | — | — | — | — |
| 45 | 3.4 | 4.7 | 4.3 | 134.5 | 54.3 | 136.5 | 47.8 | 135.2 | 42.9 |
| 46 | 3.4 | >10 | 5.2 | 134.5 | 54.3 | — | — | 134.2 | 119.3 |
| 47 | 3.4 | 4.7 | 3.4 | 134.5 | 54.3 | 136.5 | 47.8 | 134.4 | 64.0 |
| 48 | 3.4 | 4.2 | 3.5 | 134.5 | 54.3 | | | 137.3 | 47.7 |
| 49 | 3.4 | >10 | 5.6 | 141.7 | 41.9 | — | — | 141.9 | 73.4 |
| 50 | 3.4 | >10 | 9 | 134.5 | 54.3 | 136.5 | 47.8 | — | — |
| 51 | 3.4 | 4.7 | 3.4 | 134.5 | 54.3 | 136.5 | 47.8 | 134.9 | 50.7 |
| 52 | 3.4 | 4.2 | 3.5 | 134.5 | 54.3 | | | 126.9 | 62.7 |
| 53 | 3.4 | >10 | 4.1 | 134.5 | 54.3 | — | — | 137.7 | 46.1 |
| 54 | 3.4 | 4.7 | 3.4 | 134.5 | 54.3 | 136.5 | 47.8 | 138.6 | 45.0 |
| 55 | 3.4 | 4.4 | 3.8 | 141.2 | 39.6 | 146.6 | 62.0 | 138.0 | 46.2 |
| 56 | 3.4 | >10 | >10 | 141.7 | 41.9 | — | — | — | — |
| 57 | 3.4 | 4.7 | 4.1 | 141.7 | 41.9 | 134.6 | 63.0 | 149.8 | 39.3 |
| 58 | 3.4 | 4.4 | 3.6 | 141.2 | 39.6 | 146.6 | 62.0 | 138.2 | 46.1 |
| 59 | 3.4 | >10 | 3.5 | 141.7 | 41.9 | — | — | 135.5 | 52.3 |
| 60 | 3.4 | 4.7 | 3.3 | 141.7 | 41.9 | 134.6 | 63.0 | 135.1 | 54.1 |
| 61 | 3.4 | 4.4 | 3.7 | 141.2 | 39.6 | 146.6 | 62.0 | 137.7 | 49.4 |
| 62 | 3.4 | >10 | >10 | 141.7 | 41.9 | — | — | — | — |
| 63 | 3.4 | 4.7 | 3.9 | 141.7 | 41.9 | 134.6 | 63.0 | 147.6 | 40.7 |
| 64 | 3.4 | 4.4 | 3.5 | 141.2 | 39.6 | 146.6 | 62.0 | 139.4 | 45.0 |
| 65 | 3.4 | >10 | >10 | 141.7 | 41.9 | — | — | — | — |
| 66 | 3.4 | 4.7 | 3.8 | 141.7 | 41.9 | 134.6 | 63.0 | 137.4 | 53.4 |

TABLE 5-continued

Back pressure and height of valley results from functionality tests performed before and after introduction of problems and after regeneration of the columns according to the conditions listed in table 4.
RT is the retention time for DesB30 insulin and height of valley (HV) is for DesB30 insulin and the nearest impurity.

| | Back pressure (MPa) | | | Performance | | | | | |
|---|---|---|---|---|---|---|---|---|---|
| | | | | Before problems | | After problems | | After regeneration | |
| Example no. | Before problems | After problems | After regeneration | RT ml | HV mAU | RT ml | HV mAU | RT ml | HV mAU |
| 67 | 3.4 | 4.7 | 3.5 | 141.7 | 41.9 | 134.6 | 63.0 | 138.4 | 39.1 |
| 68 | 3.4 | >10 | 3.9 | 141.7 | 41.9 | 134.6 | — | 138.8 | 49.3 |

Example 69

Column Life Time-Chromatographic Solvents/Eluents

The life time of substituted silica gels may be limited by the chemical degradations of the gel by the solutions applied to the chromatographic column, e.g. buffers and regeneration solutions. Chemical degradation of substituted silica gels may be observed by the appearance of silicium in the exit from the column, or by lowering of the carbon contents of the gel showing loss of the substitution. The following experiments show the silicium appearance in column effluent and the decrease of the carbon contents of the gels during prolonged flushing with three chromatographic solutions: 20% ethanol in water, eluent 1 and eluent 2. Composition of eluent 2 is 31% w/w ethanol, 1.5% w/w KCl, 0.40% w/w $CaCl_2$, 0.15% w/w triethanol amine and pH adjusted to pH 7.4 using HCl. The composition of eluent 1 is salt, buffer, ethanol and pH 3.0.

A batch of ODDMS silica gel was packed in five 4.0×250 mm steel columns by standard procedure for packing chromatographic columns. The columns were then equilibrated with 3 CV of ethanol before continuous flushing with a chromatographic eluent was started. The five columns were then flushed with a chromatographic eluent (20% EtOH, eluent 1 or eluent 2) for 1, 3, 7, 12, and 16 days, respectively. After the appropriate flushing time each column were then equilibrated with 3 CV of ethanol and the silica gel was taken out of the columns. A sample of the spent silica gel was subjected to analysis of the carbon contents, and a sample of the spent regeneration solution was subjected to analysis for the silicium contents. The results for day no 0 is the result (carbon contents) of the silica gel used for packing the columns.

TABLE 6

Assessment of column lifetime during prolonged flushing with typical chromatographic eluents by measurement of remaining carbon and released silicium.

| | Column no | Chrom solution | Duration (days) | Measured C (%) | Measured Si (mg) | Volume (mL) | Relative C (%) |
|---|---|---|---|---|---|---|---|
| 100 Å ODDMS 4.0*250 mm | | | 0 | 19.40 | 0.00 | 0 | 100.00 |
| | 204614/15 | 20% EtOH | 1 | 19.14 | 0.05 | 136 | 98.66 |
| | 204614/16 | 20% EtOH | 3 | 19.16 | 0.13 | 425 | 98.76 |
| | 204614/17 | 20% EtOH | 7 | 19.26 | 0.31 | 1540 | 99.28 |
| | 204614/23 | 20% EtOH | 12 | 19.28 | 0.25 | 1270 | 99.38 |
| | 204614/24 | 20% EtOH | 16 | 19.27 | 0.41 | 1360 | 99.33 |
| | | | 0 | 19.40 | 0.00 | 0 | 100.00 |
| | 204614/18 | Eluent 1 | 1 | 18.67 | 0.15 | 147 | 96.24 |
| | 204614/20 | Eluent 1 | 3 | 18.85 | 0.36 | 360 | 97.16 |
| | 204614/21 | Eluent 1 | 7 | 18.76 | 0.87 | 870 | 96.70 |
| | 204614/19 | Eluent 1 | 12 | 18.64 | 1.33 | 1325 | 96.08 |
| | 204614/22 | Eluent 1 | 16 | 18.67 | 0.86 | 860 | 96.24 |

| | Column no | 20% EtOH (% v/v) | Duration (days) | Measured C (%) | Measured Si (mg) | Volume (mL) | Relative C (%) |
|---|---|---|---|---|---|---|---|
| 200 Å ODDMS 4.0*250 mm | | | 0 | 9.80 | 0.00 | 0 | 100.00 |
| | 204630/14 | 20% EtOH | 1 | 9.61 | 0.03 | 160 | 98.06 |
| | 204630/13 | 20% EtOH | 3 | 9.66 | 0.09 | 430 | 98.57 |
| | 204630/15 | 20% EtOH | 7 | 9.72 | 0.09 | 425 | 99.18 |
| | 204630/16 | 20% EtOH | 12 | 9.69 | 0.18 | 610 | 98.88 |
| | 204630/18 | 20% EtOH | 16 | 9.69 | 0.28 | 930 | 98.88 |
| | | | 0 | 9.80 | 0.00 | 0 | 100.00 |
| | 204630/19 | Eluent 2 | 1 | 9.55 | 0.13 | 125 | 97.45 |
| | 204630/17 | Eluent 2 | 3 | 9.55 | 0.40 | 400 | 97.45 |
| | 204630/20 | Eluent 2 | 7 | 9.54 | 0.85 | 850 | 97.35 |
| | 204630/21 | Eluent 2 | 12 | 9.59 | 1.29 | 1290 | 97.86 |
| | 204630/23 | Eluent 2 | 16 | 9.49 | 0.70 | 700 | 96.84 |

Example 70

Column Life Time-Regeneration Solutions Comprising Formic Acid

The life time of substituted silica gels may be limited by the chemical degradations of the gel by the solutions applied to the chromatographic column, e.g. buffers and regeneration solutions. Chemical degradation of substituted silica gels may be observed by the appearance of silicium in the exit from the column, and by lowering of the carbon contents of the gel showing loss of the substitution. The following experiments show the silicium appearance in column effluent and the decrease of the carbon contents of the gels during prolonged flushing with formic acid containing regeneration solutions. Thus, comparing to the situation using chromatographic buffers or solvents, the formic acid containing regeneration solutions are not more deteriorating on the column matrix.

A batch of ODDMS silica gel was packed in five 4.0×250 mm steel columns by standard procedure for packing chromatographic columns. Each column were then equilibrated with 3 CV 100% EtOH before continuous flushing with formic acid was started. The five columns were then flushed with a regeneration solvent being formic acid (100% or 80%) for 1, 3, 7, 12, and 16 days, respectively. After the appropriate flushing time each column were then equilibrated with 3 CV of ethanol and the silica gel was taken out of the columns. A sample of the spent silica gel was subjected to analysis of the carbon contents, and a sample of the spent regeneration solution was subjected to analysis for the silicium contents. The results for day no 0 is the result (carbon contents) of the silica gel used for packing the columns.

Example 71

Using Confocal Laser Scanning Microscopy Detecting Insulin Fibrils on Source 30Q Anion Exchanger Purpose The purpose of using Confocal laser scanning microscopy is to visual determine how effectively different regenerating solvents are in removing insulin fibrils from Source 30Q. With sophisticated image processing software allowing the opportunity to measure the area of insulin fibrils on each picture giving a more precise judgment in stead of an visual judgment of each picture The Confocal Principle The principle in using CLSM is that the sample is stained with a fluorescent dye. The stained sample is placed under the microscope and the fluorescent dye is exitated using a laser. The emitted light coming from the fluorescent dye is detected and the image formed.

Confocal laser scannings microscope is as normal confocal microscope using a laser as lightsource. The light from the laser is going through the objective of the microscope via the dichromatic beamsplitter. The dichromatic beamsplitter is a device allowing the light from the laser to go through the objective down to the sample and the emitted light coming from the sample to pass the dichromatic beamsplitter and go up to the photomultiplier tubes where the light is detected and the image is formed. Between the dichromatic beamsplitter and photomultiplier tubes is the confocal pinhole placed. The confocal pinhole works as a filter stopping all the light coming from out of focus regions in reaching the photomultiplier tubes. This means that the image there is formed comes from a very narrow focus plane. By adjusting the confocal pinhole it is possible to move the image focus plane up and down through the sample and produce a series of images along the optical (z) axis of the microscope. This series of images can be collected into 3-D image of the sample.

TABLE 7

Assessment of column lifetime during prolonged regeneration with solutions containing formic acid by measurement of remaining carbon and released silicium.

| Column type | Column no. | Formic acid (%) | Duration (days) | Measured C (%) | Measured Si (mg) | Volume (mL) | Relative C (%) |
|---|---|---|---|---|---|---|---|
| 100 Å ODDMS 4.0*250 mm | 0 | — | 0 | 19.40 | 0.00 | 0 | 100.00 |
| | 204614/7 | 100 | 1 | 19.00 | 0.82 | 124 | 97.94 |
| | 204614/5 | 100 | 3 | 18.90 | 1.46 | 510 | 97.42 |
| | 204614/6 | 100 | 7 | 18.26 | 1.95 | 620 | 99.28 |
| | 204614/3 | 100 | 12 | 18.97 | 5.63 | 1430 | 97.78 |
| | 204614/2 | 100 | 12 | 18.94 | 3.92 | 1100 | 97.63 |
| | 0 | — | 0 | 19.40 | 0.00 | 0 | 100.00 |
| | 204614/8 | 80 | 1 | 19.08 | 1.67 | 177 | 98.35 |
| | 204614/10 | 80 | 3 | 19.08 | 2.62 | 410 | 98.35 |
| | 204614/9 | 80 | 7 | 18.93 | 4.55 | 970 | 97.58 |
| | 204614/11 | 80 | 12 | 17.04 | 6.07 | 1080 | N.D. |
| | 204614/12 | 80 | 16 | 18.61 | 6.86 | 2090 | 95.93 |
| 200 Å ODDMS 4.0*250 mm | 0 | — | 0 | 9.80 | 0.00 | 0 | 100.00 |
| | 204630/8 | 100 | 1 | 9.56 | 0.62 | 85 | 97.55 |
| | 204630/5 | 100 | 3 | 9.50 | 1.77 | 510 | 96.94 |
| | 204630/6 | 100 | 7 | 9.41 | 1.02 | 800 | 96.02 |
| | 204630/3 | 100 | 12 | 9.67 | 1.31 | 1020 | 98.67 |
| | 204630/2 | 100 | 12 | 9.63 | 1.22 | 1655 | 98.27 |
| | 0 | — | 0 | 9.80 | 0.00 | 0 | 100.00 |
| | 204630/7 | 80 | 1 | 9.64 | 0.56 | 141 | 98.37 |
| | 204630/10 | 80 | 3 | 9.42 | 0.77 | 440 | 96.12 |
| | 204630/9 | 80 | 7 | 9.43 | 1.10 | 920 | 96.22 |
| | 204630/11 | 80 | 12 | 8.67 | 1.40 | 1470 | N.D. |
| | 204630/12 | 80 | 16 | 9.18 | 1.46 | 2000 | 93.67 |

Source 30Q

Source 30Q is a strong anion exchanger based on monodisperse beads with a particle size of 30 micron. The matrix consists of polystyrene/divinyl benzene. Source 30Q gives a weak autofluorescence's in the wavelength area above 650 nm. This means that is possible to see the Source 30Q particles without any staining.

Thioflavin T

The dye used for staining insulin fibrils is Thioflavin T which is known for staining amyloid proteins. Thioflavin T has a broad emission spectrum with max emission ranging from below 490 nm and above 530 nm. This means that it is possible to distinct between light coming from the insulin fibrils (green) and the autofluorescence's light coming from the particles (red).

Method for Staining Insulin Fibrils on Source 30Q 0.0385 g dry Source 30Q is put into 25-30 ml glass.

500 μl 96% ethanol is added to the Source 30Q 4.5 ml 0.05 M acetic acid adjusted to pH 3 with NaOH is added.

The mixture is mixed together by shaking the glass carefully

20 μl 116.62 mM Thioflavin T in Milli-Q-water is added

The mixture is carefully shaken for 5 min.

The sample is now stained and ready for analysing under the microscope

A small droplet of the mixture approximately 40 μl I placed in a microscopic well and put in the microscope 10 2D pictures of each sample from different places of the well was taken Equipment Microscopic Conditions Objective: 40*; oil; NA?

Laser: Argon 488 nm

Laser intensity: 100%

Confocal pinhole: 20 μm

Emission filter (No 2): 515/30M from Chroma

Emission filter (No 3): HQ650LP from Chroma

Microscope: Nikon TE300 equipped with PCM2000 confocal scanhead (photomultiplier) from Nikon.

Software: Nikon EZ2000 Viewer 2.5.77

Software used for image processing: AnalySIS 3.00

Image Processing

The area of insulin fibrils was measured on the 10 2D pictures from each sample. To ensure that each sample was treated exactly the same way the image processing was done automatically by forming a macro. The macro is shown below. The area of each individual fibril from the 10 pictures of each sample was summarized in excel worksheet. The summarized fibril area from each sample was collected in a bar chart for comparison.

Macro for Measuring Area of Fibrils:

Op.Display=1;
docActivate("picture name");
DbLoadImage( );
MaximizeContrast( );
ShadingCorrection(N*N average filter size; 3; lower limit; 1900; upper limit; 2000);
BinarizeColorImage(ColorThresholds:=NULL, Phase:=−1);
Invert( );
EdgeEnhance(size; 5; percent; 70);
SetFrame(Left:=0, Top:=0, Right:=1023, Bottom:=1023);
Detect( );
ParticleResults( );
Op.Display=6;
Option.BurnOverlay=TRUE;
SaveAs(FileName:);
docActivate("Sheet*");
SaveAs(FileName:);
Close(AskFor Save:=TRUE);

TABLE 8

Measured area of fibrils on a spent Source 30Q gel before and after regeneration of the gel using different regeneration solutions.

| Regeneration solution | Area of fibrils (random units) |
|---|---|
| None | 485 |
| None | 458 |
| NaOAc (0.25% w/w NaOAc, 0.24% w/w tris, 42.5% w/w EtOH, pH 7.5 | 154 |
| NaOH (1M) | 101 |
| HCOOH:water (50:50) | 68 |
| HCOOH (100%) | 0 |
| HCOOH:EtOH (50:50) | 0 |

Complete removal of the insulin fibrils are obtained using pure formic acid or a mixture of formic acid and ethanol. A 50:50 mixture of formic acid:water does not completely eliminate the fibrils, although this mixture is a more efficient regeneration solution than sodium hydroxide (1M).

Example 72

Standard Procedure for Regeneration of RP-HPLC Columns with Formic Acid in Production Scale The procedures described below applies to two types of columns used in four chromatographic purification steps in a production scale purification of human insulin.

Type 1 Column:

Bed height 32.5 cm

1. The column is flushed with approximately 1.5 CV 20% w/w ethanol in water with a flow rate of 4.6 CV/h in order to remove buffer salts
2. The flow direction in the column is reversed
3. The column is flushed with approximately 1.1 CV absolute ethanol with a flow rate of 4.5 CV/h
4. 1.1 CV pure formic acid is pumped onto the column at a flow rate of 2.1 CV/h
5. The flow is stopped and the column is allowed to stay with formic acid for 30 minutes
6. The column is flushed with approximately 1.1 CV absolute ethanol with a flow rate of 4.5 CV/h
7. The column is flushed with approximately 1.1 CV 20% w/w ethanol in water with a flow rate of 4.5 CV/h
8. The flow direction in the column is switched back to normal
9. The column is equilibrated with minimum 4 CV of 20% w/w ethanol in water with a flow rate of 4.6 CV/h The column is now ready for use again.

Type 2 Column:

Bed height 37.5 cm

1. The column is flushed with approximately 1.5 CV 20% w/w ethanol in water with a flow rate of 4.6 CV/h in order to remove buffer salts
2. The flow direction in the column is reversed
3. The column is flushed with approximately 1.0 CV absolute ethanol with a flow rate of 3.9 CV/h
4. 0.92 CV pure formic acid is pumped onto the column at a flow rate of 1.9 CV/h
5. The flow is stopped and the column is allowed to stay with formic acid for 30 minutes
6. The column is flushed with approximately 1.0 CV absolute ethanol with a flow rate of 3.9 CV/h 7. The column is flushed with approximately 1.0 CV 20% w/w ethanol in water with a flow rate of 3.9 CV/h
8. The flow direction in the column is switched back to normal
9. The column is equilibrated with minimum 4.0 CV of 20% w/w ethanol in water with a flow rate of 4.6 CV/h The column is now ready for use again.

On the Type 1 columns the regeneration with formic acid is carried out after every $16^{th}$ run as a preventive action to stop build up of components, increasing column back pressures and increasing pool volumes. By applying the regeneration procedure with formic acid in the chromatographic purification I step, the life time of the column bed is extended up to 2000 runs.

On the Type 2 columns regeneration with formic acid is carried out routinely after every $60^{th}$ run or if increasing back pressures, increasing pool volumes and build up of impurities is observed. By applying the regeneration procedure with formic acid the life time of the column bed is extended up to 600 runs in chromatographic purification III step and up to 900 runs in chromatographic step IV.

The column matrix used in chromatographic purification I, III and IV steps consists of octadecyldimethyl substituted silica particles (ODDMS silica). The standard procedure described applies for all types of substituted silica matrixes used in production scale.

The procedure is also used in formic acid regeneration procedures for column matrices based on Source Q material Examples of the effect at chromatographic purification III and IV are shown below.

TABLE 9

Chromatographic purification III: Effect on pool volume and back pressure.

Before regeneration with formic acid (100%)

| Pool volume (weight) | Back pressure (max. pressure over delivery pump) |
|---|---|
| 208 kg | 27 Bar |

After regeneration with formic acid (100%)

| Pool volume | Back pressure (max. pressure over delivery pump) |
|---|---|
| 165 kg | 17 Bar |

The regeneration reduces the pool volume with app. 21% and the back pressure with 37%.

FIG. 4A-B shows the effect of regeneration on preparative chromatogram for Chromatographic purification III.

By applying the formic acid regeneration an improved separation and human insulin peak form is achieved (insulin peak being the large peak starting at time 8.20 in upper figure and at time 14.02 in lower figure).

Example 73

Regeneration of DEAE Sepharose

A batch of DEAE Sepharose which had been used for a large number of purification cycles in a process for purification of human growth hormone was regenerated by pure formic acid (100% HCOOH). Before regeneration the Sepharose has a brown colour indicating deposited material on the gel. The regenerated Sepharose was much lighter in colour.

Samples of the regenerated Sepharose was compared to the Sepharose before regeneration using a calorimeter (Minolta CR-300) to quantify the colour differences, cn.f. results in table 10.

TABLE 10

Assessment of the regeneration of DEAE Sepharose when regenerated as a slurry with a regeneration solution of formic acid.

| Sepharose material analysed | Colour coordinates | | |
|---|---|---|---|
| | L (light) | A (red) | b (yellow) |
| Spent gel before regeneration | 68.81 | 2.37 | 17.22 |
| Spent gel after 3 hour regeneration | 84.99 | 0.66 | 11.55 |
| Spent gel after 24 hour regeneration | 87.94 | 0.35 | 7.64 |
| Spent gel after 24 hour regeneration where fresh regeneration solution has been applied at 12 hour. | 85.85 | 0.69 | 8.81 |
| Unspent gel, i.e. which has never been used for chromatography | 86.44 | −0.06 | 2.01 |

Example 74

Regeneration of Spent Silica Gel Containing Glucagon Aggregates

Glucagon and the glucagon-like peptides (GLP-1 and GLP-2) are particularly susceptible to aggregation where they form fibrils, i.e. aggregates of β-sheet structures. In this example a model experiment was carried out where human glucagon was loaded onto a silica column (as described in examples 1-68). The glucagon solution was allowed to stay in the column for 3 days at 30° C. in order to introduce the pressure and performance problems mimicking the problems encountered during the industrial manufacture of glucagon. The pressure over the column was measured to 3.5 MPa using eluent 2 as described in example 69 at a flow rate of 9 mL/min at 22° C.

Following a regeneration cycle using formic acid (100%) the pressure over the column was reduced to 2.67 MPa illustrating the effectiveness of formic acid as a regeneration solution.

Example 75

Column Life Time-Regeneration Solution Containing 0.1M NaOH and 60% w/w Ethanol in Water The experiment was carried out as described in example 70 except for the regeneration solution which in this experiment was alkaline ethanol as commonly used to regenerate chromatographic stationary phases.

The flow of regeneration solution was approximately 0.1 mL/min, and the experiments were terminated after 4 days as the pressure over the columns were >10 MPa. The results until break down of the columns are shown in table 11.

TABLE 11

Assessment of column life time during prolonged regeneration with a regeneration solution containing 0.1M NaOH and 60% w/w ethanol in water.

| Column type | Column no. | Duration (days) | Measured C (%) | Measured Si (mg) | Volume (mL) | Relative C (%) |
|---|---|---|---|---|---|---|
| 200 Å ODDMS 4.0*250 mm | 0 | 0 | 9.80 | 0.0 | 0 | 100 |
| | 204630/26 | 1 | 9.80 | 16.2 | 116 | 100 |
| | 204630/25 | 2 | 9.77 | 27.0 | 180 | 99.7 |
| | 204630/24 | 4 | 9.59 | 31.9 | 228 | 97.9 |

Example 76

Regeneration of XAD 1180

The lifetime of the reverse phase polymeric resin XAD 1180 used for concentrating of an insulin precursor from clarified fermentation broth was limited because of severe accumulation of hydrophobic contaminants such as colored compounds, peptides and antifoams from the fermentation. The normal regeneration cycle was based on washing with a regeneration solution containing 80% Ethanol in 0.1M citric acid, pH 3.0 followed by heating with a 5% NaOH solution at 80° C. This regeneration process was not efficient to remove accumulated contaminants.

Removal of bound antifoam (Pluronic PE 6100 and P2000) from spent resin was evaluated by experiments with different concentration and contacting time of ethanol and isopropanol in static mode and compared to a formic acid regeneration (Table 12). The formic acid treatment is superior in removing the adsorbed contaminants compared to standard industrial regeneration solvents.

TABLE 12

Efficiency of different regeneration solutions in removing adsorbed antifoam contaminants from a spent XAD 1180 chromatographic stationary phase.

| Regeneration solvent | Conc. | Time (hours) | Temp. (° C.) | Conc. of antifoam on resin (ppm) |
|---|---|---|---|---|
| Ethanol | 84% | 2 | 25 | 20023 |
| Ethanol | 92% | 2 | 25 | 13058 |
| Ethanol | 99% | 2 | 25 | 8042 |
| Ethanol | 84% | 6 | 25 | 25083 |
| Ethanol | 84% | 2 | 50 | 14712 |
| Ethanol | 99% | 6 | 50 | 9911 |
| Isopropanol | 70% | 2 | 25 | 15899 |
| Isopropanol | 99% | 2 | 25 | 3262 |
| Formic acid | 99% | 2 | 25 | 670 |

The invention claimed is:

1. A process for regenerating a silica material or a substituted silica material chromatographic stationary phase comprising contacting said silica material or a substituted silica material chromatographic stationary phase at a temperature in the range from about 0° C. to about 70° C. with a regeneration solution comprising at least one organic acid and less than about 75% w/w water, wherein said organic acid is formic acid, wherein the concentration of formic acid is at least 25% w/w, and wherein said chromatographic stationary phase is a Reverse Phase-High Pressure Liquid Chromatography (RP-HPLC) matrix.

2. The process according to claim 1, wherein the regeneration solution comprises at least one organic acid and less than about 1% w/w water.

3. The process according to claim 1, wherein said regeneration solution contains less than 0.5% water.

4. The process according to claim 1, wherein said chromatographic stationary phase is contacted with said regeneration solution inside the chromatographic column.

5. The process according to claim 4, wherein said chromatographic stationary phase is regenerated without repacking the column.

6. The process according to claim 4, wherein said chromatographic stationary phase is fluidized during said regeneration.

7. The process according to claim 4, wherein a chromatographic eluent or equilibrium buffer is displaced by a water miscible organic solvent before said chromatographic stationary phase is contacted with said regeneration solution.

8. The process according to claim 7, wherein said organic solvent is also present in the chromatographic eluent or equilibrium buffer.

9. The process according to claim 8, wherein said water miscible organic solvent is also present in the regeneration solution.

10. The process according to claim 1, wherein said chromatographic stationary phase is contacted with said regeneration solution outside the chromatographic column.

11. The process according to claim 1, wherein said chromatographic stationary phase is C16 or C18 substituted silica.

12. The process according to claim 1, wherein said chromatographic stationary phase is C4, C8 or phenyl-substituted silica.

13. The process according to claim 1, wherein said chromatographic stationary phase is contacted with said regeneration solution for at least 1 minute.

14. The process according to claim 1, wherein said chromatographic stationary phase is contacted with said regeneration solution until the pressure drop over the length of the chromatographic column at normal flow rate decreases by at least 10%.

15. The process according to claim 1, wherein contacting of said chromatographic stationary phase with said regeneration solution is performed at a temperature in the range from about 5° C. to 50° C.

16. The process according to claim 1, wherein the life time of said chromatographic stationary phase is at least 500 chromatographic cycles.

17. The process according to claim 1, wherein said process is applied to said chromatographic stationary phase for every chromatographic cycle.

18. The process according to claim 1, wherein said process is applied to said chromatographic stationary phase at least once every 100 chromatographic cycles.

* * * * *